| United States Patent [19] | [11] Patent Number: 4,652,652 |
| Matsumura et al. | [45] Date of Patent: Mar. 24, 1987 |

[54] THIAZOLYLPROPENEDICARBOXYLIC ACID HALF ESTERS AND PROCESS FOR MAKING

[75] Inventors: Hiromu Matsumura; Toshisada Yano, both of Hyogo, Japan

[73] Assignee: Shionogi & Co., Ltd., Osaka, Japan

[21] Appl. No.: 746,564

[22] Filed: Jun. 19, 1985

[30] Foreign Application Priority Data

Jul. 12, 1984 [JP] Japan ................. 59-145794

[51] Int. Cl.$^4$ ................. C07D 277/40; C07D 277/42; C07D 277/44; C07D 277/48
[52] U.S. Cl. ................. 548/194; 560/174
[58] Field of Search ................. 548/184, 110, 194

[56] References Cited

U.S. PATENT DOCUMENTS 4,298,375 11/1981 Howe et al. ................. 548/184

FOREIGN PATENT DOCUMENTS 2163431 2/1986 United Kingdom ................. 548/194

OTHER PUBLICATIONS

Hamashima, *Chemical Abstracts*, vol. 103:104789a, (1985).

*Primary Examiner*—Donald G. Daus
*Assistant Examiner*—Stephen M. Kapner
*Attorney, Agent, or Firm*—Wenderoth, Lind & Ponack

[57] ABSTRACT

A useful intermediate for synthesizing penicillins or cephalosporins {i.e., 1-(2-protected amino-4-thiazolyl)-propene-1,3-dicarboxylic acid half ester (VI)} is prepared by a process comprising (1) treating haloacetylmalonic acid ester (I) with thiourea to give 2-(2-amino-4-thiazolyl)malonic acid ester (II), (2) protecting the amino group of the latter to give 2-(2-protected amino-4-thiazolyl)malonic acid ester (III), (3) treating the product with haloalkenoic acid ester to give 1-(2-protected amino-4-thiazolyl)-2-propene-(1,1,3-tri or 1,1,3,3-tetra)carboxylic acid ester (IV), (4) hydrolyzing and decarboxylating the latter to give 1-(2-protected amino-4-thiazolyl)propene-1,3-dicarboxylic acid (V), and (5) treating the product with alcohol and a hemiesterifying reagent to give the objective 1-(2-protected amino-4-thiazolyl)propene-1,3-dicarboxylic acid half ester (VI).

5 Claims, No Drawings

THIAZOLYLPROPENEDICARBOXYLIC ACID HALF ESTERS AND PROCESS FOR MAKING

This invention relates to a process for producing aminothiazolylglutaric acid derivatives. More specifically, it relates to a process comprising (1) treating haloacetylmalonic acid ester (I) with thiourea to give 2-(2-amino-4-thiazolyl)malonic acid ester (II), (2) protecting the amino group of the latter to give 2-(2-protected amino-4-thiazolyl)malonic acid ester (III), (3) treating the product with haloalkenoic acid ester to give 1-(2-protected amino-4-thiazolyl)-2-propene-(1,1,3-tri or 1,1,3,3-tetra)carboxylic acid ester (IV), (4) hydrolyzing and decarboxylating the latter to give 1-(2-protected amino-4-thiazolyl)propene-1,3-dicarboxylic acid (V), and (5) treating the product with alcohol and a hemi-esterifying reagent to give 1-(2-protected amino-4-thiazolyl)propene-1,3-dicarboxylic acid half ester (VI).

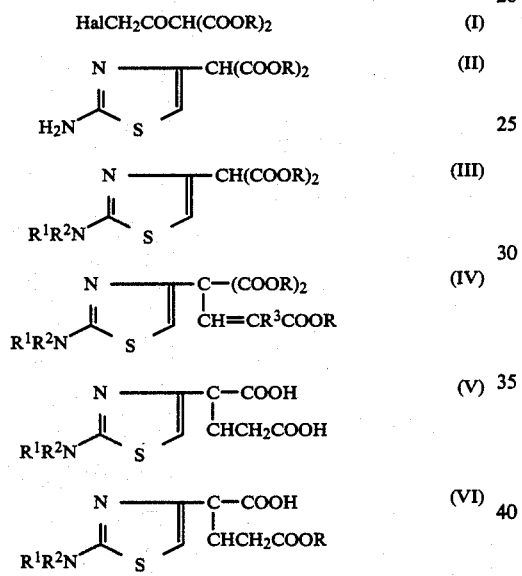

(and the double bond position isomers) (wherein Hal is halogen; R is the same or different ester forming group; $R^1$ and $R^2$ each is hydrogen or an amino-protecting group; and $R^3$ is hydrogen or COOR group)

The compounds (VI) are useful as starting materials for producing antibacterials as amido side chain of penicillins or cephalosporins and as agents for modifying amino of arylglycylpenicillins or cephalosporins.

In the above formula (I) to (VI), the ester forming group R contains 1 to 15 carbon atoms and can be (1 to 5C)alkyl; (2 to 8C)alkenyl; (1 to 5C)alkyl substituted by e.g., halogen, (1 to 5C)alkoxy, sulfonyl, etc.; benzyl; benzyl substituted by e.g., (1 to 5C)alkyl, alkoxy, nitro, phenyl; or the like easily removable ester-forming group.

The amino-protecting group $R^1$ and $R^2$ each can be (1 to 5C)alkanoyl; halo(1 to 5C)alkanoyl; (1 to 5C)alkoxycarbonyl; (8 to 15C)aralkoxycarbonyl; (13 to 20C)polyarylmethyl; (1 to 15C)enamine-forming group; tri(1 to 5C)alkylsilyl; or the like amino-protecting group of beta-lactam chemistry.

According to the process of this invention, the objective 1-(2-amino-4-thiazolyl)propene-1,3-dicarboxylic acid half esters (VI) can be produced by the following five steps. Among them, the last step, (i.e., hemi-esterification) is more important. The intermediates (II), (III), (IV), (V), and (VI) are literary unknown novel compounds.

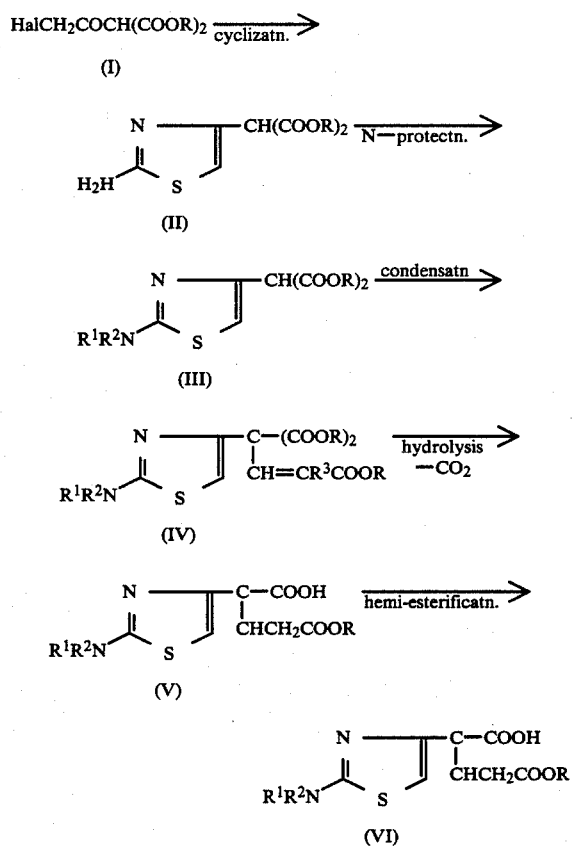

STEP 1

Thiazole-cyclization

The reaction of 2-haloacetylmalonic acid ester (I) with thiourea (1 to 5 molar equivalents) in a polar organic solvent gives 2-(2-amino-4-thiazolyl)malonic acid ester (II) in good yield. This reaction proceeds well even at room temperature and completes within 1 to 15 hours. The product is a hydrochloride. The free amine can be recovered by neutralization.

STEP 2

N-Protection

Protecting amino group of a compound (II) in a usual method affords the corresponding compound (III).

Representative protection includes acylation with halide or anhydride of the corresponding acid in the presence of base (e.g., pyridine); tritylation with the corresponding halide in the presence of hydrogen halide trapping agent; enamine formation with the corresponding carbonyl compound in the presence of acid; and other conventional amino-protections.

STEP 3

Condensation

For this condensation, compound (III) is treated with strong base (e.g., hydride, lower alkoxide, hydroxide, or the like of lithium, sodium, or potassium) (1 to 5 molar equivalents) in an aprotic solvent (e.g. ether, tetrahydrofuran, or dioxane) to give the corresponding metalo compound, and then the product is treated in situ with halo(e.g., chloro or bromo)alkenoic acid ester (1 to 3 molar equivalents) for 0.5 to 12 hours at 0° to 50° C. to give the corresponding (tri or tetra)carboxylic acid ester (IV).

STEP 4

Hydrolysis and decarboxylation

When the ester group of compound (IV) is removed to result carboxy, one of the gem-dicarboxy(s) is eliminated as carbon dioxide at −10° to 50° C. to give dicarboxylic acid (V).

Here, the removing can be done by, for example, the following conventional reactions:

(1) alkyl esters can be hydrolyzed with excess base (e.g., alkali metal hydroxide) at −10° to 50° C. for 0.5 to 10 hours to give free carboxylic acids;

(2) Highly reactive esters can be deprotected in an aqueous solution (e.g., by contacting with acid, base, buffer, ion-exchange resin). When the reactivity is low, one can deprotect by elevating it conventionally. Representative ones include a reaction of trichloroethyl ester with metal and acid; p-nitrobenzyl ester by catalytic reduction or dithionate salt; and phenacyl esters by irradiation;

(3) Aralkyl esters can be deprotected conventionally by hydrogenating with hydrogen in the presence of catalyzer (e.g., planinum, palladium, nickel);

(4) Aralkyl esters, cyclopropylmethyl esters, sulfonylethyl esters, or the like can be deprotected by e.g., solvolysis. This reaction is carried out with mineral acid, Lewis acid (e.g., aluminum chloride, tin chloride, titanium tetrachloride), sulfonic acid (e.g., methanesulfonic acid, trifluoromethanesulfonic acid), strong carboxylic acid (e.g., trifluoroacetic acid), if required in the presence of a cation scavenger;

(5) Phenacyl esters, alkenyl esters, hydroxyaralkyl esters, or the like can be deprotected with base or a nucleophilic reagent. Photochemically reactive phenacyl esters can be deprotected by irradiation of light;

(6) 2-Alkenyl esters can be deprotected with alkali metal alkanoate and palladium-triphenylphosphine complex giving the corresponding alkali metal salt; and (7) Other equivalent removing of carboxy-protecting groups.

During these reactions or work up, the said decarboxylation goes under neutral or acid condition. Thus, conventional work up gives the objective dicarboxylic acid in good yield.

STEP 5

Hemi-esterification

By conventional esterification, dicarboxylic acids (V) give diesters.

However, the action of the hemi-esterifying agent and alcohol gives half ester (VI) in good yield.

For example, dicarboxylic acid (V) is dissolved in an aprotic inert solvent (e.g., hydrocarbon or halohydrocarbon solvent) and mixed with alcohol (to be esterified) and the hemi-esterifying reagent which is acid (e.g., mineral acid (e.g., hydrochloric acid, sulfuric acid, phosphoric acid, perchloric acid), Lewis acid (e.g., phosphorus halide, thionyl halide, silyl halide, tin halide, titanium halide), sulfonic acid (e.g., methanesulfonic acid, ethanesulfonic acid, trifluoromethanesulfonic acid, benzenesulfonic acid, toluenesulfonic acid, bromobenzenesulfonic acid), dehydrating reagent (e.g., phosphorus pentoxide), or the like) preferably in the absence of base, at −10° to 80° C. (especially −5° to 40° C.) for 0.3 hour to 12 days to esterify only 3-carboxy giving half ester (VI) in good yield.

The said synthetic methods are carried out usually at −70° to 100° C. (especially −20° to 50° C.) for 10 minutes to 10 hours. These can conventionally be done in a solvent and if required under dry condition.

The reaction solvent can be a hydrocarbon (e.g., pentane, hexane, octane, benzene, toluene, xylene), halohydrocarbon (e.g., dichloromethane, chloroform, carbon tetrachloride, dichloroethane, trichloroethane, chlorobenzene), ether (e.g., diethyl ether, methyl isobutyl ether, anisole, dioxane, tetrahydrofuran), ketone (e.g., acetone, methyl ethyl ketone, cyclohexanone), ester (e.g., ethyl acetate, isobutyl acetate, methyl benzoate), nitrohydrocarbon (e.g., nitromethane, nitrobenzene), nitrile (e.g., acetonitrile, benzonitrile), amide (e.g., formamide, acetamide, dimethylformamide, dimethylacetamide, hexamethylphosphorotriamide), sulfoxide (e.g., dimethyl sulfoxide), carboxylic acid (e.g., formic acid, acetic acid, propionic acid), organic base (e.g., diethylamine, triethylamine, pyridine, picoline, collidine, quinoline), alcohol (e.g., methanol, ethanol, propanol, hexanol, octanol, benzyl alcohol), water, or the like industrial solvent or a mixture thereof. In some cases, excess reagent can serve as a solvent for the reaction.

The objective products can be obtained from the reaction mixture by removing contaminants (e.g., unreacted starting materials, by-products, solvents) by a conventional method (e.g., extraction, evaporation, washing, concentration, precipitation, filtration, drying) and worked up conventionally (e.g., by adsorption, elution, distillation, precipitation, separation, chromatography).

Following Examples illustrate the embodiments of this invention.

Physical constants of the products are listed on Tables 4 to 7. In the tables, IR shows wave numbers in Kaiser scale and NMR shows delta values in ppm scale and J values in Hz scale.

The amounts are given in parts (by weight) or equivalents (molar) per the beta-lactam starting material. In the work up, all concentration are done under reduced pressure. The physical constants of the products are identified with those of compounds prepared by an alternative route. The abbreviations used in the examples and tables are as follows:

BOC = tertiary-butoxycarbonyl,
Cbz = benzyloxycarbonyl,
Et = ethyl,
Me = methyl,
Ms = methanesulfonyl,
Ph = phenyl, and
THF = tetrahydrofuran.

EXAMPLE 1

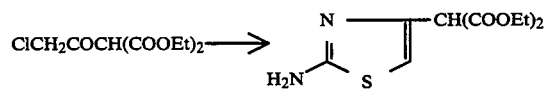

To a solution of 2-(chloroacetyl)malonic acid diethyl ester in ethanol (8 parts) is added thiourea (1.9 equivalents). After stirring at room temperature for 2 hours, the mixture is let stand overnight. The reaction mixture is concentrated, diluted with water, and neutralized with aqueous sodium hydrogen carbonate to give 2-(2-amino-4-thiazolyl)malonic acid diethyl ester. Yield: 79.2%. mp. 99.5°–100.5° C.

IR(CHCl$_3$)$\nu$: 3475, 3390, 2970, 1725 cm$^{-1}$.

NMR(CDCl$_3$)$\delta$: 1.25 (t, J=6.6 Hz, 6H), 4.23 (q, J=6.6 Hz, 4H), 4.65 (s, 1H), 5.64 (brs, 2H), 6.54 (s, 1H).

EXAMPLE 2-1

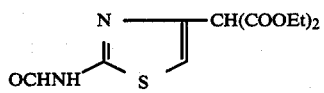

A solution of 2-(2-amino-4-thiazolyl)malonic acid diethyl ester in a mixture of acetic anhydride (6 parts) and formic acid (6 parts) is stirred at 0° C. for 1 hour. The reaction mixture is concentrated in vacuum, diluted with ethyl acetate, washed with diluted hydrochloric acid, aqueous sodium hydrogen carbonate, and water, dried, and concentrated in vacuum to give 2-(2-formamido-4-thiazolyl)malonic acid diethyl ester. Yield: 70%.

EXAMPLE 2-2

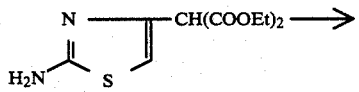

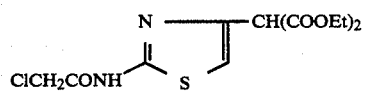

To a solution of 2-(2-amino-4-thiazolyl)malonic acid diethyl ester in N,N-dimethylformamide (10 parts) is added monochloroacetyl chloride (1.3 equivalents) under ice cooling. After stirring under ice cooling for 30 minutes and at room temperature for 1 hour, the reaction mixture is diluted with ethyl acetate and water, washed with water, dried, and concentrated in vacuum to give 2-(2-monochloroacetamido-4-thiazolyl)malonic acid diethyl ester. Yield: 99.6%.

EXAMPLE 2-3

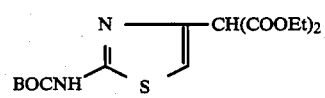

To a solution of 2-(2-amino-4-thiazolyl)malonic acid diethyl ester in t-butyl pyrocarbonate (2.25 equivalents). After stirring at 80° C. overnight, the mixture is diluted with ethyl acetate, washed with diluted hydrochloric acid, aqueous sodium hydrogen carbonate, and water, dried and concentrated under vacuum to give 2-(2-t-butoxycarbonylamino-4-thiazolyl)malonic acid diethyl ester. Yield: 73.3%.

EXAMPLE 2-4

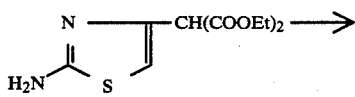

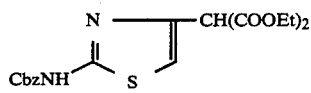

To a solution of 2-(2-amino-4-thiazolyl)malonic acid diethyl ester in dichloromethane (24 parts) are added pyridine (2 equivalents) and benzyl chlroformate (2 equivalents) at 0° C. After stirring for 30 minutes, the reaction mixture is washed with water, dried, and concentrated in vacuum to give 2-(2-benzyloxycarbonylamino-4-thiazolyl)malonic acid diethyl ester. Yield: 71.3%.

EXAMPLE 2-5

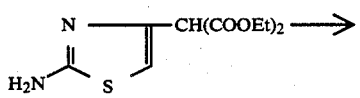

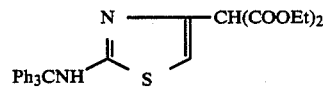

To a solution of 2-(2-amino-4-thiazolyl)malonic acid diethyl ester in dichloromethane (15 parts) are added trityl chloride (1.05 equivalents) and triethylamine (1.05 equivalents) under nitrogen at 0° C. After stirring at room temperature for 24 hours, the reaction mixture is poured onto diluted hydrochloric acid and extracted with ethyl acetate. The extract is washed with water, dried, and concentrated in vacuum to give 2-(2-tritylamino-4-thiazolyl)malonic acid diethyl ester. Yield: 98.2%.

EXAMPLE 3-1

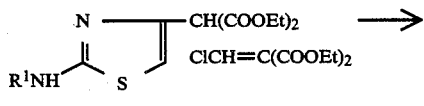

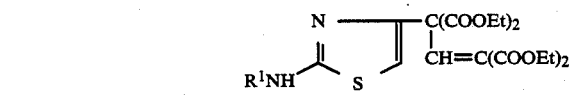

To a solution of 2-(2-protected amino-4-thiazolyl)malonic acid diethyl ester in tetrahydrofuran (5 to 40 parts) is added sodium hydride (2 to 3 equivalents). After stirring at 0° C. for 5 to 30 minutes, the produced solution of the 2-sodiomalonate is mixed with chloromethylidenemalonic acid diethyl ester (1 to 2 equivalents). After stirring at room temperature for 1 to 10 hours, the reaction mixture is treated with diluted hydrochloric acid and ethyl acetate. The separating organic layer is taken, washed with aqueous sodium hydrogen carbonate and water, dried, concentrated, and purified by chromatography to give 1-(2-protected amino-4-thiazolyl)propene-1,1,3,3-tetracarboxylic acid tetraethyl ester. Yield: 10 to 70%.

The reaction conditions are listed on Table 1.

EXAMPLE 3-2

In a manner similar to above but substituting tetrahydrofuran with dioxane or dimethoxyethane, the objective tetracarboxylic acid ester can be produced in nearly the same yield.

EXAMPLE 4-1

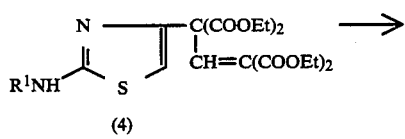

(4)

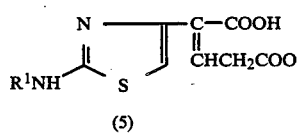

(5)

To a solution of 1-(2-protected amino-4-thiazolyl)-propene-1,1,3,3-tetracarboxylic acid tetraethyl ester in tetrahydrofuran (2 to 10 parts) are added water (5 to 30 parts) and sodium hydroxide (1 to 30 equivalents). After stirring at room temperature for 30 minutes to 10 hours, the reaction mixture is washed with ethyl acetate, acidified with hydrochloric acid, and extracted with ethyl acetate. The extract solution is washed with water, dried, and concentrated to give 1-(2-protected amino-4-thiazolyl)propene-1,3-dicarboxylic acid. Yield: 50 to 75%.

The reaction conditions are listed on Table 2.

EXAMPLE 4-2

The same dicarboxylic acid is formed under the same condition but substituting the solvent of Example 4-1 by methanol or ethanol.

EXAMPLE 5

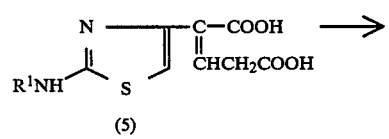

(5)

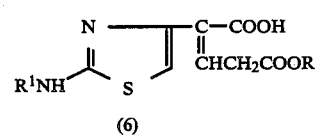

(6)

A mixture of 1-(2-(Protected amino-4-thiazolyl)propene-1,3-dicarboxylic acid in a solvent (5 to 30 parts), alcohol (4 to 10 equivalents), and a catalyzer (1 to 10 equivalents) is let react for 1 to 100 hours at 0° to 40° C. The mixture is diluted with ethyl acetate and water, washed with water, aqueous sodium hydrogen carbonate, and hydrochloric acid, dried, and concentrated. The residue is crystallized from methanol to give the corresponding half-ester. Yield: 50 to 90%.

The reaction conditions are listed on Table 3.

EXAMPLE 6

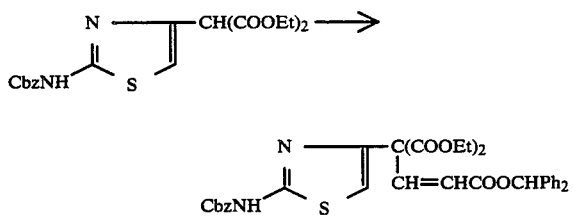

To a solution of 2-(2-benzyloxycarbonylamino-4-thiazolyl)malonic acid diethyl ester in tetrahydrofuran (20 parts) are added sodium hydride (2.35 equivalents) and a solution of trans-3-chloroacrylic acid diphemylmethyl ester (1.2 equivalents) in tetrahydrofuran (8 parts) under ice cooling. After stirring at 35° to 40° C. for 12.5 hours, the mixture is diluted with ethyl acetate and diluted hydrochloric acid, washed with water, dried, and concentrated. The residue is chromatographed over silica gel. The fraction eluted with a mixture of benzene and ethyl acetate (15:1) is crystallized from ethyl acetate to give 3-diphenylmethoxycarbonyl-1-(2-benzyloxycarbonylamino-4-thiazolyl)-2-propene-1,1-dicarboxylic acid diethyl ester.

IR(CHCl$_3$)$\nu$: 3390, 2960, 1730, 1635 cm$^{-1}$.

NMR(CDCl$_3$)$\delta$: 1.73 (t, J=6.6 Hz, 6H), 4.25 (q, J=6.6 Hz, 4H), 5.25 (s, 2H), 5.81 (d, J=15.8 Hz, 1H), 6.93 (s, 1H), 7.25~7.45 (m, 16H), 7.60 (d, J=15.8 Hz, 1H), 8.07 (brs, 1H).

TABLE 1

| Condition of the condensation. | | | | | |
|---|---|---|---|---|---|
| R$^1$ | CHO | ClCH$_2$CO | BOC | Cbz | Ph$_3$C |
| THF (part) | 22 | 20 | 23 | 18 | 18 |
| NaH (equiv.) | 2.48 | 2.39 | 2.43 | 2.46 | 2.50 |
| Na—salt (min.) | 15 | 20 | 20 | 10 | 15 |
| reagent (equiv.) | 1.46 | 1.30 | 1.14 | 1.40 | 1.30 |
| condensation (hour) | 1 | 2 | 3 | 1.5 | 5 |
| yield (%) | 32.7 | 62.1 | 43.2 | 67.4 | 13 |

TABLE 2

Condition of the hydrolysis.

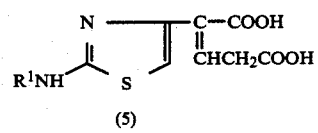

| $R^1$ | CHO | ClCH$_2$CO | BOC | Cbz | Cbz/R=Me |
|---|---|---|---|---|---|
| THF (part) | 5.26 | 3.53 | 2.29 | 6.40 | 5.73 |
| NaOH (equiv.) | 24 | 12.5 | 12.5 | 10 | 5.15 |
| water (part) | 26 | 11.8 | 11.5 | 20 | — |
| hydrolysis (min.) | 300 | 40 | 180 | 180 | 90 |
| yield (%) | 8 | 46.6 | 73.8 | 47.9 | 81.3 |

TABLE 4

Physical constants of

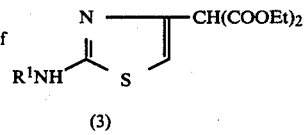

| $R^1$ | IR(CHCl$_3$)$\nu$:cm$^{-1}$ | NMR(CDCl$_3$) $\delta$:ppm |
|---|---|---|
| CHO | 3380, 3160, 1740, 1725, 1685. mp 73° | 1.23(t,J=7Hz,6H),4.20(q,J=7Hz,4H),4.77(s,1H), 7.06(s,1H),8.72(s,1H),11.65 (brs,1H). |
| ClCH$_2$CO | 3500, 2950, 1750, 1725, 1680. | 1.25(t,J=7.5Hz,6H),4.23(q,J=7.5Hz,4H),4.27(s,2H), 4.73(s,1H),7.10(s,1H),9.65 (br,1H). |
| BOC | 3420, 1750, 1730 (CCl$_4$). | 1.23(t,J=7Hz,6H),1.54(s,9H),4.20(q,J=7Hz,4H), 4.89(s,1H),6.99(s,1H),9.10 (brs,1H). |
| Cbz | 3380, 3140, 2950, 1725. mp. 80° C. | 1.22(t,J=6.9Hz,6H),4.16(q,J=6.9Hz,4H),5.08(s,1H), 5.29(s,2H),7.04(s,1H), 7.2~7.5(m,5H). |
| Ph$_3$C | 3615, 3405, 2975, 1730. | 1.24(t,J=7.2Hz,6H),4.18(q,J=7.2Hz,4H),4.65(s,1H), 6.40(s,1H),6.61(brs,1H), 7.29(brs,15H). |

TABLE 3

Condition of the half-esterification.

(TMSC = Me$_3$SiCl)

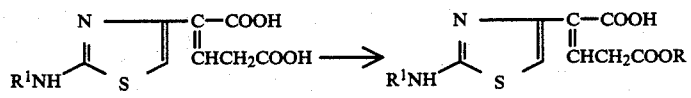

| $R^1$ | CHO | CHO | ClCH$_2$CO | ClCH$_2$CO | BOC | Cbz | | | | |
|---|---|---|---|---|---|---|---|---|---|---|
| R | PhCH$_2$ | PhCH$_2$ | PhCH$_2$ | CH$_3$ | PhCH$_2$ | Me | Me | t-C$_4$H$_9$ | PhCH$_2$ | PhCH$_2$ |
| ROH (equiv.) | 9.0 | 9.28 | 10.7 | 10 | 10 | 27 part | 15 part | 10 | 9.63 | 4.82 |
| solvent | CH$_2$Cl$_2$ | CH$_2$Cl$_2$ | CH$_2$Cl$_2$ | CH$_2$Cl$_2$ | CH$_2$Cl$_2$ | CH$_3$OH | CH$_2$Cl$_2$ | CH$_2$Cl$_2$ | CH$_2$Cl$_2$ | CH$_2$Cl$_2$ |
| (part) | 11.2 | 13.2 | 10.9 | 7.8 | 13.8 | 27.5 | 15 | 8.28 | 7.32 | 9.14 |
| catalyst | PCl$_3$ | TMSC | SOCl$_2$ | SOCl$_2$ | SOCl$_2$ | TiCl$_4$ | HCl | P$_2$O$_5$ | HCl | PCl$_6$ |
| (equiv.) | 1.0 | 2.6 | 1.50 | 1.2 | 1.2 | 1.8 | 7.2 | 1.0 | 7.2 | 1.10 |
| temperature | rt | rt | rt | rt | rt | 0° C. | rt | rt | rt | rt |
| time (hr) | 1.5 | 1.5 | 1.5 | 1.5 | 1.5 | 0.3 | 0.5 | 20 | 96 | 7 |
| yield (%) | 65 | 61 | 81 | 96 | 70 | 100 | 90 | 16 | 59 | 73 |

| $R^1$ | Cbz | | | | | | | |
|---|---|---|---|---|---|---|---|---|
| R | PhCH$_2$ | PhCH$_2$ | PhCH$_2$ | PhCH$_2$ | p-MePhCH$_2$ | p-MeOPhCH$_2$ | CH$_2$=CHCH$_2$ | CH$_2$=CHCH$_2$ |
| ROH (equiv.) | 5 | 9.63 | 9.3 | 9.63 | 10 | 5 | 10 | 10 |
| solvent | CH$_2$Cl$_2$ | CH$_2$Cl$_2$ | CH$_2$Cl$_2$ | CH$_2$Cl$_2$ | CH$_2$Cl$_2$ | CH$_2$Cl$_2$ | CH$_2$Cl$_2$ | CH$_2$Cl$_2$ |
| (part) | 5.5 | 7.32 | 2.76 | 11.0 | 20 | 5 | 13.8 | 13.8 |
| catalyst | POCl$_3$ | SOCl$_2$ | TiCl$_4$ | TMSC | SOCl$_2$ | MsOH | SOCl$_2$ | MsOH |
| (equiv.) | 1.3 | 1.20 | 2.0 | 2.6 | 1.2 | 1.2 | 1.2 | 1.3 |
| temperature | rt | rt | rt | rt | rt | 0~5° C. | 0° C.~rt | 0~5° C. |
| time (hr) | 16 | 2 | 3.5 | 3 | 3 | 120 | 5 | 20 |
| yield (%) | 86 | 83 | 60 | 80 | 80 | 43 | 88 | 90 |

| $R^1$ | Cbz | | | | | |
|---|---|---|---|---|---|---|
| R | MeCH=CHCH$_2$ | CH$_2$=CMe—CH$_2$ | CH$_2$=CHCHMe | Me$_2$C=CHCH$_2$ | Me$_2$C=CHCH$_2$* | PhCH=CHCH$_2$ |
| ROH (equiv.) | 10 | 5 | 5 | 5 | 5 | 5 |
| solvent | CH$_2$Cl$_2$ | CH$_2$Cl$_2$ | CH$_2$Cl$_2$ | CH$_2$Cl$_2$ | CH$_2$Cl$_2$ | CH$_2$Cl$_2$ |
| (part) | 13.8 | 13.8 | 13.8 | 8.3 | 13.8 | 13.8 |
| catalyst | SOCl$_2$ | MsOH | MsOH | MsOH | MsOH | MsOH |
| (equiv.) | 1.2 | 1.3 | 1.3 | 1.3 | 1.3 | 1.3 |
| temperature | rt | 0~5° C. | 0~5° C. | 0~5° C. | rt | 0~5° C. |
| time (hr) | 24 | 240 | 144 | 168 | 96 | 72 |
| yield (%) | 88 | 86 | 88 | 75 | 44 | 71 |

*CH$_2$=CHCMe$_2$OH is used as ROH

TABLE 5

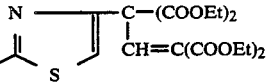

Physical constants of (4)

| $R^1$ | IR(CHCl$_3$)$\nu$:cm$^{-1}$ | NMR(CDCl$_3$)$\delta$:ppm |
|---|---|---|
| CHO | 3380, 3150, 2970, 1745, 1710(sh). | 1.11~1.37(m, 12H), 4.12(q, J=7.5Hz, 2H), 4.20(q, J=7.5Hz, 4H), 4.28(q, J=7.5 Hz, 2H), 7.41(s, 1H), 7.70(s, 1H), 8.65(brs, 1H). |
| ClCH$_2$CO | 3375, 2980, 1740, 1720, 1690, 1650. | 1.17, 1.23, 1.31(3×t, J=8Hz, 12H), 3.85~4.32(m, 8H), 4.21(s, 2H), 7.45(s, 1H), 7.61(s, 1H), 10.12(brs, 1H). |
| BOC | 3400, 2965, 1730, 1635, mp. 126° C. | 1.10~1.38(m, 12H), 4.07(q, J=6.7Hz, 2H), 4.25(q, J=6.7Hz, 2H), 4.26(q, J=6.7 Hz, 2H), 7.42(s, 1H), 7.78(s, 1H), 7.97(brs, 1H). |
| Cbz | 3380, 2950, 1730, 1640. | 1.10~1.40(m, 12H), 4.02(q, J=7.5Hz, 2H), 4.20(q, J=7.5Hz, 6H), 5.21(s, 2H), 7.34(s, 5H), 7.77(s, 1H). |
| Ph$_3$C | 1730, 1635. | 1.05~1.40(m, 12H), 3.96(q, J=7.5Hz, 2H), 4.15(q, J=7.5Hz, 2H), 4.25(q, J=7.5 Hz, 2H), 6.48(brs, 1H), 6.85(s, 1H), 7.25(brs, 15H), 7.75(s, 1H). |
| H | 1730, 1595. mp. 113~114° C. | 1.1~1.4(m, 12H), 3.95~4.4(m, 8H), 5.41(brs, 2H), 7.02(s, 1H), 7.75(s, 1H). |

TABLE 6

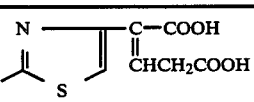

Physical constants of (5)

| $R^1$ | IR(Nujol)$\nu$:cm$^{-1}$ | NMR(CD$_3$SOCD$_3$)$\delta$:ppm |
|---|---|---|
| BOC cis | 3120, 1700, 1675. dp 153~154° C. | 1.50(s, 9H), 3.45(d, J=7.5Hz, 2H), 7.00(t, J=7.5Hz, 1H), 7.13(s, 1H). |
| BOC trans | 3150, 1700, 1630, 1600. dp 165~167° C. | 1.49(s, 9H), 3.41(d, J=7.5Hz, 2H), 6.89(t, J=7.5Hz, 1H), 7.08(s, 1H). |
| Cbz | 3200, 1738, 1715, 1690. dp 169~172° C. | 3.44, 3.50, (2×d, J=8Hz, 2H), 5.25(s, 2H), 7.07, 7.35(2×t, J=8Hz, 1H), 7.12(s, 1H), 7.38(brs, 5H) [CDCl$_3$+CD$_3$OD] |
| HCO | 3400, 1718, 1690, 1630, 1550. dp 168° C. | 3.45, 3.63(2×d, J=7.5Hz, 2H), 7.14, 7.32(2×t, J=7.5Hz, 1H), 7.23, 7.25(2×s, 1H), 8.51(s, 1H) [CDCl$_3$+CD$_3$OD]. |
| ClCH$_2$CO— | 3100, 1720, 1685, 1620. dp 153~155° C. | 3.45(d, J=8Hz, 2H), 4.37(s, 2H), 6.97, 7.05(2×t, J=8Hz, 1H), 7.23, 7.27(2×s, 1H). |

TABLE 7

Physical constants of (6)

| $R^1$ | R | IR(Nujol)$\nu$:cm$^{-1}$ | NMR(CD$_3$SOCD$_3$)$\delta$:ppm |
|---|---|---|---|
| BOC | t-Bu | 1725, 1620, 1545 [CHCl$_3$] | 1.45(s, 9H), 1.53(s, 9H), 3.30, 3.64(d+d, J=7Hz, 2H), 6.98, 7.04(s+s, 1H), 6.99, 7.32(t+t, J=7Hz, 1H) [CDCl$_3$]. |
| BOC | Bzl | 3160, 1740, 1724, 1700, 1678, 1255, 1168. | 3.95(d, J=7.5Hz, 2H), 5.50(s, 2H), 7.26(t, J=7.5Hz, 1H), 7.30(brs, 1H), 7.49(s, 1H), 7.75(s, 5H), 11.86(brs, 1H). |
| HCO (1 cis: 2 trans) | t-Bu | 3150, 3100, 1720, 1690, 1635. mp. 185~188° C. | 1.40(s, 9H), 3.43(d, J=7Hz, 2H), 6.89, 7.00(2×t, J=7Hz, 1H), 7.20, 7.26 (2×s, 1H), 8.48(s, 1H). |
| HCO | Bzl | 1735, 1680, 1620. dp 153~155° C. | 3.69(d, J=7Hz, 2H), 5.12(s, 2H), 7.17(t, J=7Hz, 1H), 7.21(s, 1H), 7.32 (s, 5H), 8.46(s, 1H). |
| ClCH$_2$CO | Me | nd | 3.39(d, J=7.5Hz, 2H), 3.70(s, 3H), 4.24(s, 2H), 7.11(s, 1H), 7.23(t, J=7.5Hz, 1H), 9.37(brs, 2H) [CDCl$_3$]. |
| ClCH$_2$CO | Bzl | 1726, 1685, 1160. dp 155° C. | 3.95, 4.01(2×d, J=7.5Hz, 2H), 4.71(s, 2H), 5.45, 5.47(2×s, 2H), 7.28, 7.40(2×t, J=7.5Hz, 1H), 7.58, 7.65(2×s, 1H), 7.70(s, 5H), 12.9(brs, 1H). |
| Cbz | Me | 3400~2300, 1740, 1550. | 3.58~3.73(m, 2H), 3.63(s, 3H), 5.27(s, 2H), 7.03~7.46(m, 7H). |
| Cbz (trans) | t-Bu | 3160~2200, 1720, 1680, 1635. mp. 169~171° C. | 1.42(s, 9H), 3.53(d, J=7Hz, 2H), 5.29(s, 1H), 7.27(t, J=7Hz, 1H), 7.35 (s, 1H), 7.30~7.50(m, 5H). |
| Cbz (cis) | t-Bu | nd | 1.44(s, 9H), 3.53(d, J=7Hz, 2H), 5.27(s, 2H), 7.13(t, J=7Hz, 1H), 7.24 (s, 1H), 7.30~7.47(m, 5H) [CDCl$_3$]. |
| Cbz (2 cis: 1 trans) | Me— Bzl | 3150~2050, 1720, 1670, 1620, 1570. mp. 160~163° C. | 2.33(s, 3H), 2.53, 2.70(2×d, J=8Hz, 2H), 5.11(s, 2H), 5.26(s, 2H), 6.99~ 7.40(m, 10H) [CDCl$_3$—CD$_3$OD]. |
| Cbz (2 cis: 3 trans) | Bzl | 1725, 1675, 1620, 1575. mp. 164~166° C. | 3.51, 3.73(2×d, J=7Hz, 2H), 5.13(s, 2H), 5.26(s, 2H), 7.06, 7.10(2×s, 1H), 7.0~7.5(m, 11H) [CDCl$_3$—CD$_3$OD]. |
| Cbz | PMB | 1720, 1575, 1515. mp. 145~148° C. | 3.80(d, J=8Hz, 2H), 3.90(s, 3H), 5.20(s, 2H), 5.33(s, 2H), 7.00(s, 1H), 6.85~7.60(m, 10H) [CDCl$_3$—CD$_3$OD]. |
| Cbz (1 cis: 2 trans) | CH$_2$ CH CH$_2$ | 3515, 2480(br), 1736, 1549, 1305, 1086 (CHCl$_3$) mp. 122~130° C. | 3.35(d, J=8Hz, 4/3H), 3.68(d, J=8Hz, 2/3H), 4.56(d, J=6Hz, 2H), 5.11~ 5.37(m, 4H), 5.65~6.15(m, 1H), 6.90~7.41(m, 7H), 9.82(bs, 2H). [CDCl$_3$]. |
| Cbz (1 cis: 5 trans) | CHMe CH CH$_2$ | 3420, 2500(br), 1732, 1549, 1302, 1087 (CHCl$_3$) mp. 127~131° C. | 1.16(d, J=7Hz, 1/2H), 1.29(d, J=7Hz, 5/2H), 3.46(d, J=8Hz, 5/3H), 3.68 (d, J=8Hz, 1/3H), 5.05~5.49(m, 3H), 5.16(s, 2H), 5.66~6.02(m, 1H), 7.08~ 7.57(m, 7H) [CDCl$_3$—CD$_3$OD]. |
| Cbz | CH$_2$ | 3420, 1736, 1548, 1307, | 1.73(s, 3H), 3.52(d, J=8.5Hz, 11/10H), 3.73(d, J=8.5Hz, 9/10H), 4.54(s, 2 |

TABLE 7-continued

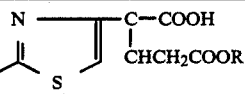

Physical constants of $R^1NH$ ... S ...

| $R^1$ | R | IR(Nujol)ν:cm$^{-1}$ | NMR(CD$_3$SOCD$_3$)δ:ppm |
|---|---|---|---|
| (9 cis: 11 trans) | CMe CH$_2$ | 1085 (CHCl$_3$) mp. 120~123° C. | H), 4.95(brs, 2H), 5.26(s, 2H), 6.99~7.46(m, 7H) [CDCl$_3$—CD$_3$OD]. |
| Cbz (1 cis: 4 trans) | CH$_2$ CH CHMe | 3415, 1732, 1548, 1304, 1076 (CHCl$_3$) mp. 139~142° C. (decomp.). | 1.67(d, J=6Hz, 3H), 3.44(d, J=8Hz, 8/5H), 3.64(d, J=8Hz, 2/5H), 4.49(d, J=6Hz, 2H), 5.23(s, 2H), 5.35~6.05(m, 2H), 7.05~7.41(m, 7H) [CDCl$_3$—CDCl$_3$]. |
| Cbz (1 cis: 2 trans) | CH$_2$ CH CMe$_2$ | 3175, 2520(br), 1732, 1659, 1071. mp. 167~168° C. (decomp.). | 1.98(s, 3H), 2.03(s, 3H), 3.82(d, J=8Hz, 4/3H), 3.86(d, J=8Hz, 2/3H), 4.87(d, J=7Hz, 2H), 5.64(s, 2H), 5.52~5.71(m, 1H), 7.21(t, J=8Hz, 1/3H), 7.65~7.69(m, 5+2/3H) [CD$_3$SOCD$_3$—CD$_3$OD(external TMS)]. |
| Cbz | CH$_2$ CH CHPh | nd | TLC [EtOAc/CHCl$_3$(1:1)]: Rf=0.2 |

What we claim is:

1. A process for producing aminothiazolylpropanedicarboxylic acid derivatives which comprises (1) treating haloacetylmalonic acid ester (I) with thiourea to give 2-(2-amino-4-thiazolyl)malonic acid ester (II), (2) protecting the amino group of the latter to give 2-(2-protected amino-4-thiazolyl)malonic acid ester (III), (3) treating the product with haloalkenoic acid ester to give 1-(2-protected amino-4-thiazolyl)-2-propene-(1,1,3-tri or 1,1,3,3-tretra)carboxylic acid ester (IV), (4) hydrolyzing and decarboxylating the latter to give 1-(2-protected amino-4-thiazolyl)propene-1,3-dicarboxylic acid (V), and (5) treating the product with alcohol and a hemi-esterifying reagent to give 1-(2-protected amino-4-thiazolyl)propene-1,3-dicarboxylic acid half ester (VI) as follows:

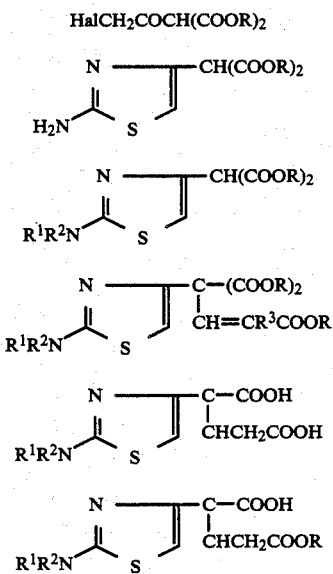

and the double bond position isomers, thereof, wherein Hal is halogen;

R is the same or a different ester-forming group selected from the group consisting of 1C to 5C alkyl, 2C to 8C alkenyl, or benzyl, all optionally substituted by halogen, 1C to 5C alkyl, 1C to 5C alkoxy, nitro, or phenyl;

R$^1$ and R$^2$ each is hydrogen or an amino-protecting group selected from the group consisting of 1C to 5C alkanoyl, 1C to 5C haloalkanoyl, 1C to 5C alkoxycarbonyl, 8C to 15C aralkoxycarbonyl, 13C to 20C polyarylmethyl, or tri-(1C to 5C)-alkylsilyl; and R$^3$ is hydrogen or a COOR group.

2. A process for producing a 1-(2-protected amino-4-thiazolyl)-propene-1, 3-dicarboxylic acid half ester (VI), which comprises treating a 1-(2-protected amino-4-thiazolyl)propene-1, 3-dicarboxylic acid (V) with an alcohol (VII) and an acid selected from a mineral acid, a lower alkanesulfonic acid, an arylsulfonic acid, a Lewis acid, or phosphorus pentoxide, in which formulas (V), (VI) and (VII) are as follows:

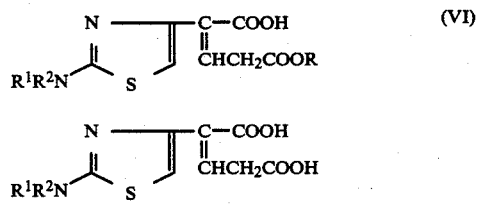

wherein R, R$^1$, and R$^2$ are as defined in claim 1.

3. A process claimed in claim 2, wherein the reaction is carried out in a solvent selected from hydrocarbon, halohydrocarbon, the reagent alcohol, and a mixture of these.

4. A process claimed in claim 2, wherein the reaction is carried out at 0° to 40° C. for a 1 to 200 hours period.

5. 2-(1-Amino-4-thiazolyl)malonic acid ester, 1-(2-amino-4-thiazolyl)propene-(1,1,3-tri or 1,1,3,3-tetra)carboxylic acid ester, or N-protected derivative thereof represented by the following formula:

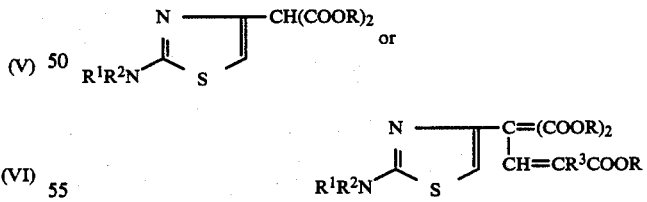

wherein R is the same or different ester-forming group selected from the group consisting of 1C to 5C alkyl, 2C to 8C alkenyl, or benzyl, all optionally substituted by halogen, 1C to 5C alkyl, 1C to 5C alkoxy, nitro, or phenyl;

R$^1$ and R$^2$ each is hydrogen or an amino-protecting group selected from the group consisting of 1C to 5C alkanoyl, 1C to 5C haloalkanoyl, 1C to 5C alkoxycarbonyl, 8C to 15C aralkoxycarbonyl, 13C to 20C polyarylmethyl, or tri-(1C to 5C)-alkylsilyl; and R$^3$ is hydrogen or a COOR group.

* * * * *